United States Patent [19]
Eibl et al.

[11] Patent Number: 5,614,493
[45] Date of Patent: Mar. 25, 1997

[54] USE OF HUMAN PROTEIN C FOR PREVENTION AND TREATMENT OF DEPOSITIONS OF THROMBOCYTES

[75] Inventors: Johann Eibl; Hans-Peter Schwarz, both of Vienna, Austria; Miguel Lozano-Molero, Barcelona, Spain

[73] Assignee: Immuno AG, Vienna, Austria

[21] Appl. No.: 261,914

[22] Filed: Jun. 16, 1994

[30] Foreign Application Priority Data

Jun. 18, 1993 [DE] Germany ............... 43 20 294.2

[51] Int. Cl.$^6$ .................. A61K 35/14; A61K 35/16; A61K 38/36; C07K 14/475
[52] U.S. Cl. ............... 514/12; 514/8; 514/822; 530/380; 530/829; 530/830; 530/381
[58] Field of Search ............. 514/12, 8, 21, 514/822; 530/380, 381, 829, 830

[56] References Cited

U.S. PATENT DOCUMENTS

| | | | |
|---|---|---|---|
| 4,160,025 | 7/1979 | Eibl et al. | 514/21 |
| 4,297,344 | 10/1981 | Schwinn et al. | 530/381 |
| 4,379,085 | 4/1983 | Williams | 530/381 |
| 4,404,187 | 9/1983 | Schwinn et al. | 530/381 |
| 4,405,603 | 9/1983 | Schwinn et al. | 530/381 |
| 4,440,679 | 4/1984 | Fernandes et al. | 530/363 |
| 4,480,029 | 10/1984 | Dolana | 435/5 |
| 4,585,654 | 4/1986 | Landaburu et al. | 530/395 |
| 4,640,834 | 2/1987 | Eibl et al. | 424/176.1 |
| 4,673,733 | 6/1987 | Chandra et al. | 530/344 |
| 4,814,435 | 3/1989 | Schwarz et al. | 530/383 |
| 4,857,320 | 8/1989 | Wittwer | 424/94.63 |
| 4,904,641 | 2/1990 | Eibl et al. | 514/2 |
| 4,909,251 | 3/1990 | Seelich | 606/213 |
| 4,923,815 | 5/1990 | Tanaka et al. | 435/183 |
| 5,084,274 | 1/1992 | Griffin et al. | 424/94.64 |
| 5,118,794 | 6/1992 | Grangeorge et al. | 530/363 |
| 5,132,406 | 7/1992 | Uemura et al. | 530/390.1 |
| 5,143,838 | 9/1992 | Kraus et al. | 435/214 |
| 5,143,901 | 9/1992 | Schwarz et al. | 514/2 |
| 5,151,499 | 9/1992 | Kameyama et al. | 530/381 |
| 5,186,945 | 2/1993 | Shanbrom | 424/529 |
| 5,316,766 | 5/1994 | Baldus et al. | 24/94.63 |
| 5,330,907 | 7/1994 | Philapitsch et al. | 435/217 |
| 5,371,195 | 12/1994 | Grandgeorge et al. | 530/383 |
| 5,410,022 | 4/1995 | Eibl et al. | 530/383 |

FOREIGN PATENT DOCUMENTS

| | | |
|---|---|---|
| B-83927/82 | 12/1982 | Australia . |
| B-39961/89 | 1/1992 | Australia . |
| B-30329/89 | 8/1992 | Australia . |
| 350726 | 6/1979 | Austria . |
| 390801 | 7/1990 | Austria . |
| 391808 | 12/1990 | Austria . |
| 2183/91 | 11/1991 | Austria . |
| 0015055 | 9/1980 | European Pat. Off. . |
| 0035204 | 9/1981 | European Pat. Off. . |
| 0050061 | 4/1982 | European Pat. Off. . |
| 0053338 | 6/1982 | European Pat. Off. . |
| 0052827 | 6/1982 | European Pat. Off. . |
| 0077870 | 5/1983 | European Pat. Off. . |

(List continued on next page.)

OTHER PUBLICATIONS

Kirschstein et al. "Impaired Fibrinolytic Capacity & Tissue Plasminogen Activator Release in Patients w/Restenosis after Percutaneous Transluminal Coronary Angioplasty (PTCA)" Thromb. Haemostas 62(2):772–775 1989.

DeStefano et al. "Replacement Therapy w/ a Purified Protein C Concentrate During Initiation of Oral Anticoagulation in Severe Protein C Congenital Deficiency" Thromb. Haemostas 70(2):247–249 1993.

(List continued on next page.)

*Primary Examiner*—Mindy Fleisher
*Assistant Examiner*—Nancy J. Degen
*Attorney, Agent, or Firm*—Foley & Lardner

[57] ABSTRACT

The use of human Protein C for the prevention and treatment of deposition or aggregation of thrombocytes, microparticles of thrombocytes, and leucocytes is described. In addition, an improved method for the extra-corporeal treatment of body fluids is disclosed.

9 Claims, 6 Drawing Sheets

FOREIGN PATENT DOCUMENTS

| | | |
|---|---|---|
| 0094611 | 11/1983 | European Pat. Off. . |
| 0099445 | 2/1984 | European Pat. Off. . |
| 0117064 | 8/1984 | European Pat. Off. . |
| 0124506 | 11/1984 | European Pat. Off. . |
| 0124044 | 11/1984 | European Pat. Off. . |
| 0131740 | 1/1985 | European Pat. Off. . |
| 0142059 | 5/1985 | European Pat. Off. . |
| 0144709 | 6/1985 | European Pat. Off. . |
| 0159311 | 10/1985 | European Pat. Off. . |
| 0173242 | 3/1986 | European Pat. Off. . |
| 0177836 | 4/1986 | European Pat. Off. . |
| 0191606 | 8/1986 | European Pat. Off. . |
| 0197554 | 10/1986 | European Pat. Off. . |
| 0196761 | 10/1986 | European Pat. Off. . |
| 0215548 | 3/1987 | European Pat. Off. . |
| 0278487 | 8/1988 | European Pat. Off. . |
| 0287028 | 10/1988 | European Pat. Off. . |
| 0292003 | 11/1988 | European Pat. Off. . |
| 0307847 | 3/1989 | European Pat. Off. . |
| 0324729 | 7/1989 | European Pat. Off. . |
| 0326014 | 8/1989 | European Pat. Off. . |
| 0341103 | 11/1989 | European Pat. Off. . |
| 0343275 | 11/1989 | European Pat. Off. . |
| 1527261 | 12/1989 | European Pat. Off. . |
| 0345246 | 12/1989 | European Pat. Off. . |
| 0318201 | 2/1990 | European Pat. Off. . |
| 0378208 | 7/1990 | European Pat. Off. . |
| 0416890 | 3/1991 | European Pat. Off. . |
| 0439156 | 7/1991 | European Pat. Off. . |
| 0443875 | 8/1991 | European Pat. Off. . |
| 0519901 | 12/1992 | European Pat. Off. . |
| 0519900 | 12/1992 | European Pat. Off. . |
| 0528701 | 2/1993 | European Pat. Off. . |
| 0534812 | 3/1993 | European Pat. Off. . |
| 0541507 | 5/1993 | European Pat. Off. . |
| 0406216 | 10/1993 | European Pat. Off. . |
| 0575054 | 12/1993 | European Pat. Off. . |
| 2916711 | 11/1980 | Germany . |
| 82/03871 | 11/1982 | WIPO . |
| 83/04371 | 12/1983 | WIPO . |
| 88/08710 | 11/1988 | WIPO . |
| 90/07524 | 7/1990 | WIPO . |
| WO90/10712 | 9/1990 | WIPO . |
| 90/12028 | 10/1990 | WIPO . |
| WO90/15613 | 12/1990 | WIPO . |

OTHER PUBLICATIONS

Ehrlich et al. "Recombinant human protein C derivatives: altered response to calcium resulting in enhanced activation by thrombin," *EMBO Journal* 9(8):2367–2373 (1990).

O. Taby et al. "Inhibition of Activated Protein C by Aprotinin and the Use of the Insolubilized Inhibitor for its Purification," *Thrombosis Research* 59:27–35 (1990).

Bajaj et al. "A Procedure for Isolation of Human Protein C and Protein S," *Preparative Biochemistry*, 13(3):191–214, (1983).

Henriksson et al. "Effects of Leukocytes, Plasmin and Thrombin on Clotting Factors," *Thrombosis Research* 16:301–312 (1979).

Cho et al. "Active Site Mapping of Bovine and Human Blood Coagulation Serine Proteases . . . " *Biochemistry* 23:647 (1984).

Loscalzo, J. "An Overview of Thrombolytic Agents," *Chest* 97(4):117S–123S (Apr. 1990, supplement).

Comp et al. "Activation of Protein C In Vivo," *J. Clin Invest.* 70:127–134 (Jul., 1982).

Eisenberg et al. "Differential Effects of Activation of Prothrombin by Stratokinase . . . ," *Thrombosis Research* 50:707–717 (1988).

Okajima et al. *Thrombosis and Haemostasis* 63:48–53, (1990).

Köhler et al. "Continuous cultures of fused cells secreting antibody of predefined specificity," *Nature* 256:495–497 (Aug. 1975).

Collen et al. "Thrombolysis with Human Extrinsic (Tissue–Type) Plasminogen Activator in Rabbits with Experimental Jugular Vein Thrombosis," *J. Clin. Invest.*, 71:368–376 (Feb. 1983).

Gruber et al. "Inhibition of Thrombus Formation by Infusion of Activated Protein C with Urokinase in a Primate Thrombosis Model," *Blood* 74(7, suppl 1) Abstract No. 176 (Nov. 1989).

Yang et al. "Plasminogen, Alpha$_2$–Antiplasmin, and Protein C Decline Following Infusions of Recombinant Tissue Plasminogen Activator," *Seminars in Thrombosis and Hemostasis* 16(3):242–2442 (1990).

Gulba et al. "Increased Thrombin Levels During Thrombolytic Therapy in Acute Myocardial Infarction," *Circulation*, 83(3):937–944 (Mar. 1991).

"Advances in Applied Biotechnology Series," vol. 11, Protein C and Related Anticoagulants (Bruley and Drohan eds.), Gulf Publishing Co., Houston, London, Paris, Tokyo (1990), pp. 83–89.

Hirahara et al. "Synergistic Effect of Antithrombin III, Activated Protein C and Heparin on the Inhibition of the Tissue Thromboplastin–Mediated Coagulation," *Chem. Pharm. Bull.* 37(3):692–96 (1989).

Brummelhuis, "Preparation of the Prothrombin Complex", *Methods of Plasma Protein Fractionation*, pp. 117–125 (1980).

Mannucci, "Outbreak of Hepatitis A Among Italian Patients with Haemophilia", *The Lancet*, vol. 339, p. 819 (Mar. 28, 1992).

Pape et al., "Standardization of an in vitro Red Blood Cell Test for Evaluating the Acute Cytotoxic Potential of Tensides", *Arzneim.–Forsch./Drug Res.* 40., pp. 498–502 (1990).

Vogelaar et al., "Contributions to the Optimal Use of Human Blood", *Vox Sanguinis*, vol. 26, pp. 118–127 (1974).

Mannucci et al., "Low Risk of Viral Infection After Administration of Vapor–Heated Factor VIII Concentrate", *Transfusion*, vol. 32, pp. 134–138 (1992).

Müller, "New Ion Exchangers for the Chromatography of Biopolymers", *Journal of Chromatography*, 510, pp. 133–140 (1990).

Hellmut Hartert, "Thrombosis and Bleeding Disorders", Academic Press, New York, 1971, pp. 70–76.

T. Seelich, "Fibrinogen, Fibrin and Fibrin Glue, Side Effects of Therapy with Clotting Factor Concentrates", F.K. Schlattauer Verlag, Stuttgart, New York, 1980, pp. 199–208.

H. Suomela, "Preparation and Properties of a Therapeutic Factor IX Concentrate", 1977, Vox Sanguinis, Journal of Blood Transfusion, Immunohaemotology and Immunopathology, vol. 33, pp. 37–50.

R. Clemens, "Wie Virussicher Sind Blut und Plasmaderivate?", Z. Allg. Med. 65, 429–433 (1989) pp. 429–433.

Commission of the European Communities, "AD HOC Working Party on Biotechnology/Pharmacy" 111/8115/89–EN Final, pp. 1–15.

D.B. Rubinstein, M.D., "Inability of Solvent–Detergent (S–D) Treated Factor VIII Concentrate to Inactivate Parvoviruses and Non–Lipid Enveloped Non–A, Non–B Hepatitis Virus in Factor VIII Concentrate: Advantages to Using Sterilizing 100 C Dry Heat Treatment", American Journal of Hematology 35:142, 1990.

A.M. Prince, "The Development of Virus–Free Labile Blood Derivatives". Eur. J. Epidemiol., Jun. 1987, pp. 103–118.

Chemical Abstracts, vol. 111, No. 27, 1989, No. 22, 201439j.

Chemical Abstracts, vol. 114, Feb. 4, 1991, No. 5, 39082a.

Rozenberg, XII International Congress on Blood Transfusion Abstracts, Aug. 17–23, 1969, Moscow, pp. 473–475.

Chemical Abstracts, Pharmaceuticals, vol. 84, No. 16, Apr. 19, 1976, US Abstract No. 111640n.

Signa Catalog, 1992, p. 1470.

Santander et al., "Role of Activated Protein C on Platelet Aggregation Induced by Thrombin", Acta Physiologica Latino–Americana, vol. 33, No. 2, pp. 59–62 (1983).

Harris et al., "Protein S Is Required for Bovine Platelets to Support Activated Protein C Binding and Activity", The Journal of Biological Chemistry, vol. 260, No. 4, pp. 2007–2010 (1985).

Jennings et al., "Analysis of Human Platelet Glycoproteins IIb–IIIa and Glanzmann's Thrombasthenia in Whole Blood by Flow Cytometry", Blood, vol. 68, No. 1., (Jul. 1986).

Shattil et al., "Changes in the Platelet Membrane Glycoprotein IIb–IIIa Complex During Platelet Activation", The Journal of Biological Chemistry, vol. 260, No. 20, pp. 11107–11114 (Sep. 1985).

Berman et al,. "A Platelet Alpha Granule Membrane Protein That Is Associated with the Plasma Membrane After Activation", Journal for Clinical Investigation, vol. 78, pp. 130–137 (Jul. 1986).

Johnston et al., "Structural and Biosynthetic Studies of the Granule Membrane Protein, GMP–140, from Human Platelets and Endothelial Cells", The Journal of Biological Chemistry, vol. 264, No. 3, pp. 1816–1823 (1989).

Nieuwenhuis et al,. "Studies With a Monoclonal Antibody Against Activated Platelets: Evidence That a Secreted 53,000 – Molecular Weight Lysosome–like Granule Protein Is Exposed on the Surface of Activated Platelets in the Circulation", Blood, vol. 70, No. 3, pp. 838–845 (Sep. 1987).

Baumgartner, "Platelet Interaction with Collagen Fibrils in Flowing Blood", Thrombos. Haemostas., vol. 37, pp. 1–16 (1977).

"Recent Advances and New Developments in Hemostaseology", Haemostasis, 4th Congress of the Society on Thrombosis and Haemostasis (GTH), Abstract 11, p. 8 (Oct. 1986).

Derwent Abstract Accession No. 93–128866/46, JP, 05064588 (Teijin Ltd.) 19 Mar. 1993.

Derwent Abstract Accessoin No. 92–058691/08, EP, 471660 (Immuno AG) 19 Feb. 1992.

Richardson et al., Nature 360: 261–264 (19 Nov. 1992).

ON PARAMETER STATISTICS

TWO PARAMETER ANALYSIS

USE OF HUMAN PROTEIN C FOR PREVENTION AND TREATMENT OF DEPOSITIONS OF THROMBOCYTES

The invention relates to a new range of application of human Protein C and a pharmaceutical preparation for the treatment of thrombo-embolic conditions.

BACKGROUND OF THE INVENTION

Protein C is a vitamin K-dependent protein that is synthesized in the liver and circulates as an inactive zymogen in a concentration of 4 mg/l. It is transformed by the thrombin-thrombomodulin complex into the active serine protease (activated Protein C) on the vessel wall surface (endothelium). It is known that activated Protein C has profibrinolytic properties. It also has anticoagulatory effects because it inactivates Factor Va, the co-factor for the Factor Xa-induced prothrombin activation (thrombin formation), and Factor VIIIa, the co-factor for Factor IXa-induced Factor X activation, by proteolysis.

The activation of Protein C in vivo constitutes a negative feedback reaction of thrombin generation. In order to develop optimal biological activity, a co-factor (Protein S) is necessary.

In the European patent application EP 0 406 216 a pharmaceutical preparation is described which contains Protein S, optionally, in combination with activated Protein C, and can be employed for the treatment or prevention of thrombosis and thrombo-embolic complications.

According to EP 0 519 900 the use of a Protein C-containing pharmaceutical preparation together with a thrombolytically effective substance for the treatment of thrombosis and for the prevention of re-occlusion is possible. It was found that during the thrombolysis therapy a deficiency of Protein C results wherefore the substitution with Protein C is recommended.

The effect of the inactive zymogen of Protein C differs fundamentally from the active enzyme, activated Protein C.

Activated Protein C enables the prevention of arterial thrombosis or stenosis, preferably in combination with a thrombolytically effective agent (tissue plasminogen activator, tPA); for this, see EP 0 318 201.

It is also known that in blood platelet-enriched plasma (PRP) activated Protein C suppresses platelet aggregation which is induced by thrombin activation. However, a higher concentration of activated Protein C leads to an opposite effect, namely to the aggregation of the blood platelets (E. N. Santander et al., Acta Physiologica Latino-Americana 3.3. (2), 1983).

Activated or stimulated blood platelets possess the glycoprotein IIb–IIIa complex which functions as a receptor for various adhesion molecules. Among the adhesion proteins that bind to GP IIb–IIIa of stimulated blood platelets are fibrinogen, von Willebrand Factor, and fibronectin. It is supposed that a tri-peptide sequence, namely Arg-Gly-Asp (RGD), of the adhesion proteins binds to the receptor. Among the proteins with a RGD sequence are also human Protein C and activated Protein C. However, the interaction of Protein C or activated Protein C with blood platelets is uncertain. It was found, for example, that activated Protein C binds to non-stimulated blood platelets in the presence of Protein S, and by this, the inactivation of Factor Va is potentiated. Protein C does not, however, bind to the blood platelets (J. Biol. Chem., 260 (4), 2007–10, 1985).

With the help of flow cytometry for thrombocytes, surfaces of thrombocytes can be examined. Flow Cytometry allows the fast and sensitive analysis of receptor proteins on a single cell. During the examinations, a flow rate from 400–1000 thrombocytes per second is employed. The size of the thrombocytes is expressed by the light scattering. By the use of antibodies coupled with fluorescein-isothiocyanate, the binding of ligands (adhesion proteins) on a thrombocyte can be measured (description of the method in Blood, 86 (1), 173–179, 1986).

The binding of fibrinogen to stimulated thrombocytes leads finally to the aggregation and/or deposition of these on injured endothelium and therewith to occlusion of the wound. Thrombo-embolic complications or stenosis are also attributable to the binding of fibrinogen to stimulated thrombocytes. For example, balloon angioplasty leads to an injury of the endothelium and therewith to a predisposition for arterial restenosis.

SUMMARY OF THE INVENTION

The object of the invention is to extend the range of application of human Protein C and to make a preparation available that can be administered for the prevention and treatment of the deposition and/or aggregation of thrombocytes.

The object is solved according to the invention by a new use of human Protein C for the production of a pharmaceutical preparation which is suitable for the prevention and treatment of deposition and/or aggregation of thrombocytes, microparticles of thrombocytes (dust), and leucocytes with pro-coagulatory activity. Protein C prevents the deposition on vessel surfaces or vessel stenoses, in particular on injured, virus-infected or damaged endothelium and/or on exposed subendothelium or artificial vessel surfaces or vessel prostheses with or without endothelium. It was found that the binding of fibrinogen on stimulated blood platelets can be prevented by the addition of human Protein C in a dose-dependent manner. PRP was stimulated by addition of adenosine diphosphate (ADP) and the fibrinogen binding measured. The addition of a fluorescein-isothiocyanate-coupled antibody against fibrinogen allowed the detection of the fibrinogen found in PRP bound on thrombocytes by measurement on the flow cytometer. The prevention of the fibrinogen binding on stimulated thrombocytes was all the more surprising because activated Protein C had no influence on the fibrinogen binding. Therefore, it is probable that the RGD sequence in a protein can not alone be responsible for the prevention of the fibrinogen binding.

DETAILED DESCRIPTION OF PREFERRED EMBODIMENTS

Figure 1A:
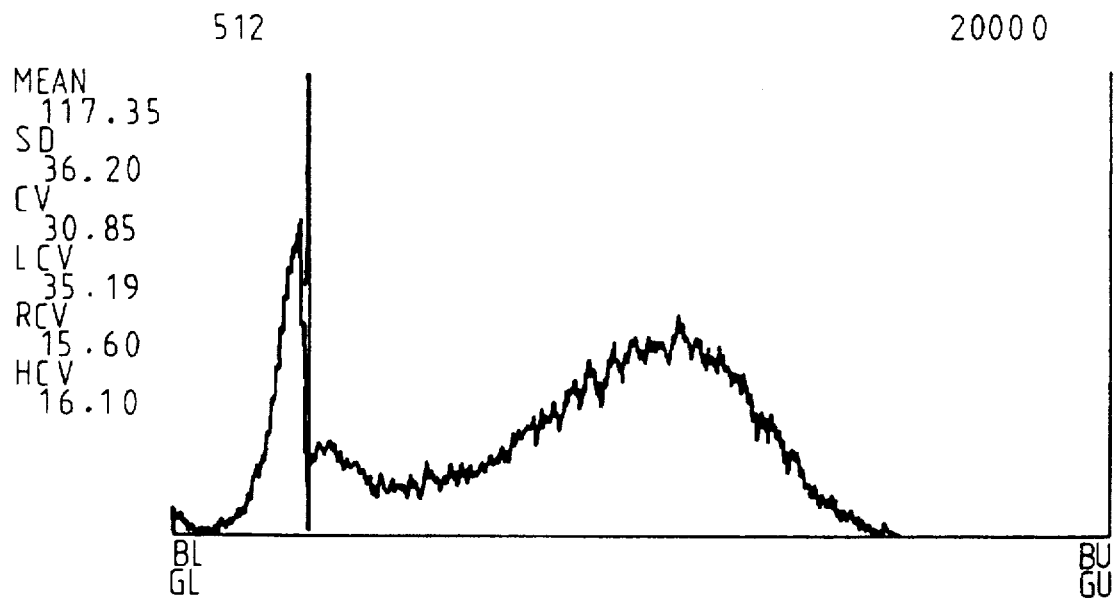
FIG. 1 depicts fluorescence data from a fibrinogen binding assay in platelet-enriched plasma after stimulation with adenosine diphosphate.

Experiments with monoclonal antibodies (for example, PAC-1, an IgM antibody that only recognizes the activated form of the IIb–IIIa complex; S. J. Shattil, J. Biol. Chem. 260, 11107, 1985) make it clear that the GP IIb–IIIa complex exposed by the activation of thrombocytes is not bound by the antibodies in the presence of Protein C. A competitive binding of protein C to GP IIb–IIIa is therefore supposed. Instead of PAC-1, however, the use of other monoclonal antibodies against thrombocyte activation-dependent epitopes is also possible, for example, PADGEM (J. Clin. Invest., 78, 130, 1986), GMP (J. Biol. Chem., 264, 1816, 1989), and 2.28 (Blood 70, 838, 1987). Hence, the binding site of fibrinogen is blocked. In contrast to the other adhesion proteins, the aggregation of the thrombocytes is not promoted, but instead prevented by this. Experiments with a perfusion chamber demonstrated that Protein C prevents the adhesion of thrombocytes in a rabbit aorta that is flushed with blood. The endothelium is stabilized then in the presence of Protein C, whereby the adhesion of stimulated thrombocytes is prevented.

Protein C, as a native protein, as a derivative thereof, or mutant with an RGD sequence can be used according to the invention. Protein C in its inactive form as a zymogen is usable. This has the advantage that the protein does not have to be activated in order to prevent the fibrinogen binding or von Willebrand Factor binding on stimulated blood platelets. Therefore, Protein C can also be used according to the invention in certain conditions, like homocyteinurea, diabetes, or uremia, in which the endogenous activation of Protein C is inhibited. The zymogen Protein C also does not have the disadvantage of the activated Protein C, namely that it leads in a high concentration to an aggregation of the thrombocytes.

The experiments with the help of flow cytometry confirm that human Protein C is suitable above all for the prevention of arterial restenosis. According to the invention, Protein C can therefore be used with all interventions of angioplasty, but also with use of a catheter, in order to prevent negative interactions with stimulated thrombocytes among themselves, with leucocytes, and with the endothelium.

On the basis of the found mechanism of action of Protein C, a process according to the invention is possible for the extra-corporeal treatment of body fluids, such as blood or ascites, with which the deposition and/or aggregation of thrombocytes in a circulation apparatus should be prevented. This method finds application, for example, in a dialysis apparatus or an artificial kidney.

By the following examples, the invention is further described.

Fibrinogen binding to activated PRP 10 ml of blood was drawn in citrate. PRP was obtained by conventional centrifugation. The addition of ADP resulted in the stimulation of thrombocytes. Subsequently, a fluorescein-isothiocyanate-coupled antibody against fibrinogen was added, and the fibrinogen bound on thrombocytes was determined by measurement on the flow cytometer (FACScan®, Becton Dickinson). The fibrinogen binding was determined by the Green Fluorescence Intensity (one parameter statistics, x-axis "Log Green Fluorescence" (bound antifibrinogen), y-axis "Number of Cells") as well as by the light scattering (two parameter analysis, x-axis "Log-Green Fluorescence", y-axis "Log-Light Scatter" (size of the thrombocytes)).

Figure 1B:
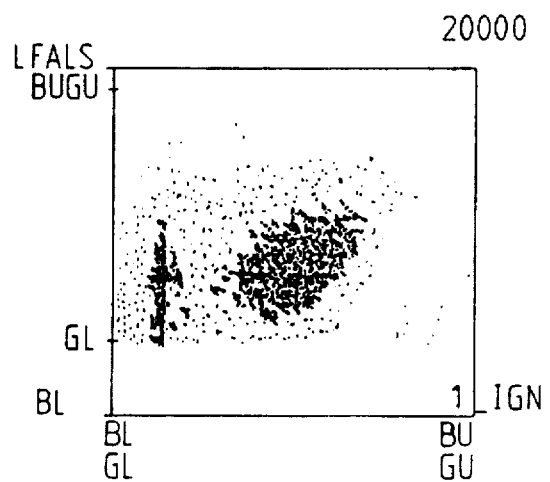
Figure 2A:
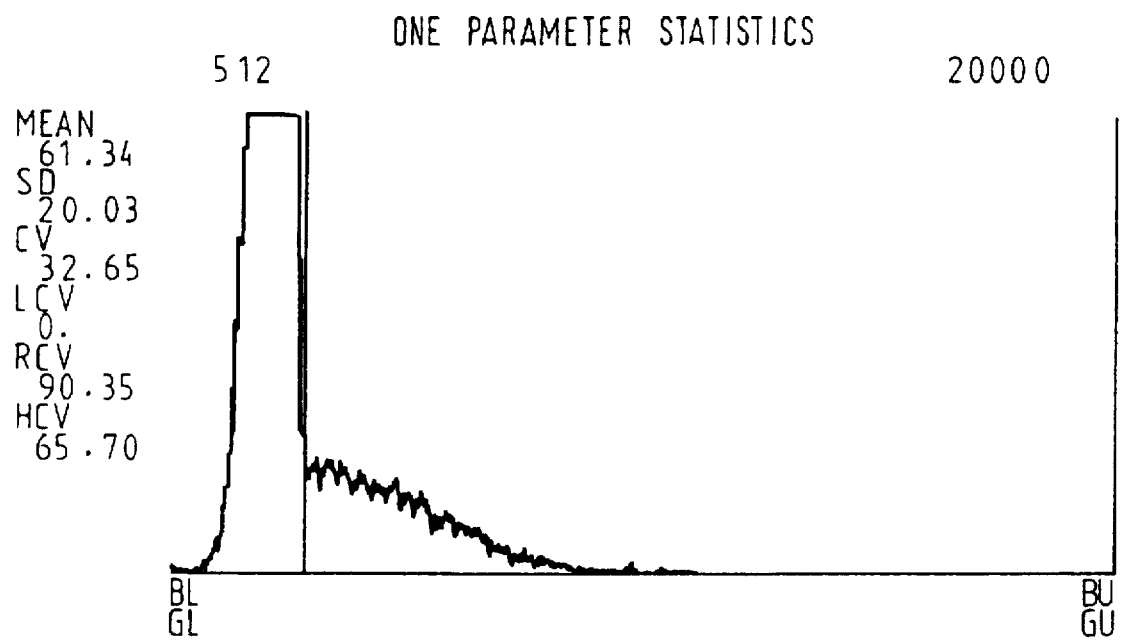
FIG. 2 depicts fluorescence data from a fibrinogen binding assay after stimulation with adenosine diphosphate in the presence of protein C in a concentration approximately four times greater than found in plasma.
Figure 2B:
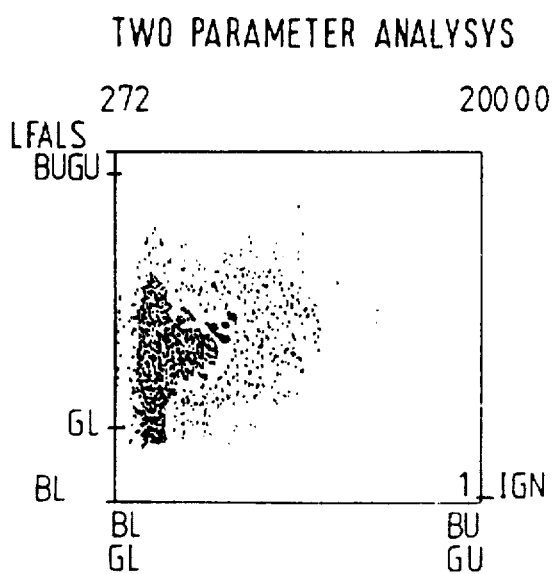
Figure 3A:
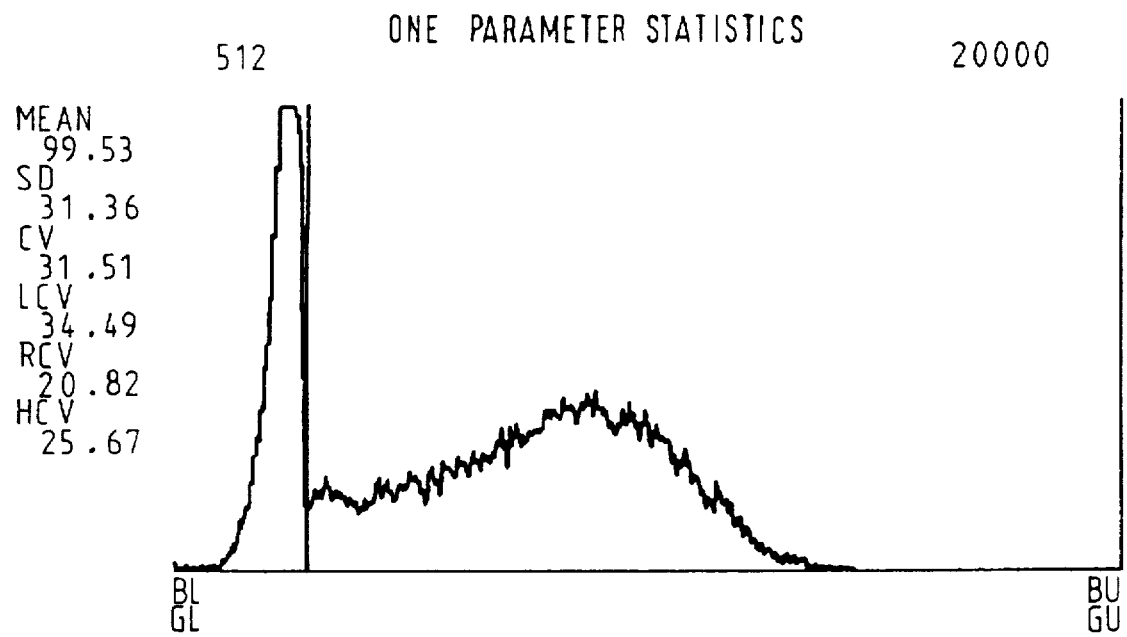
FIG. 3 depicts a fluorescence data from an assay that shows that activated protein C does not decrease fibrinogen binding on thrombocytes.
Figure 3B:
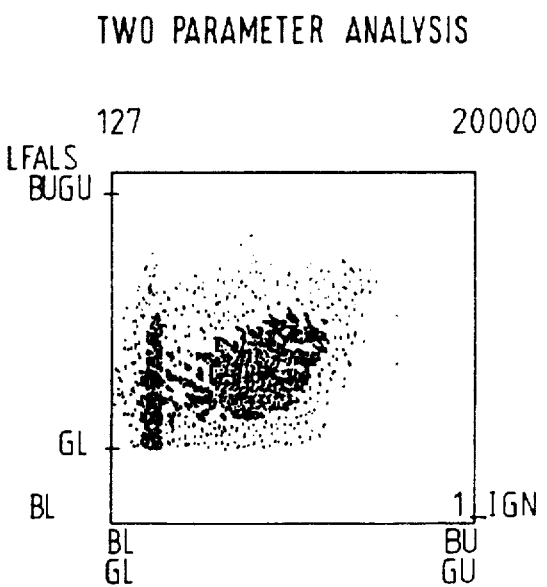
Figure 4A:
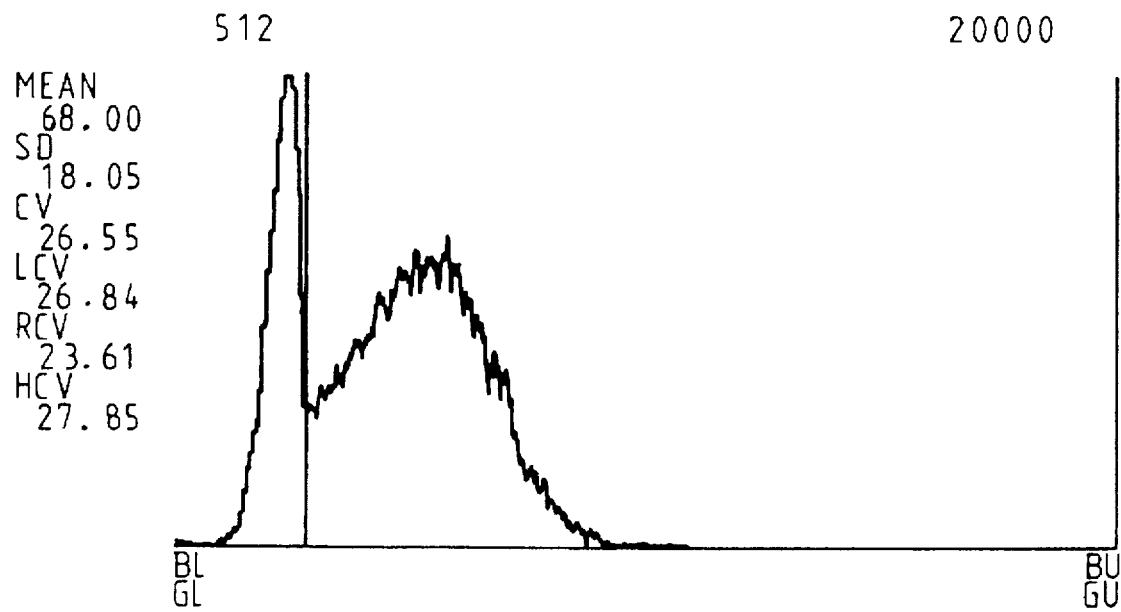
FIG. 4 depicts the binding of PAC-1 to platelet-enriched plasma/adenosine diphosphate.
Figure 4B:
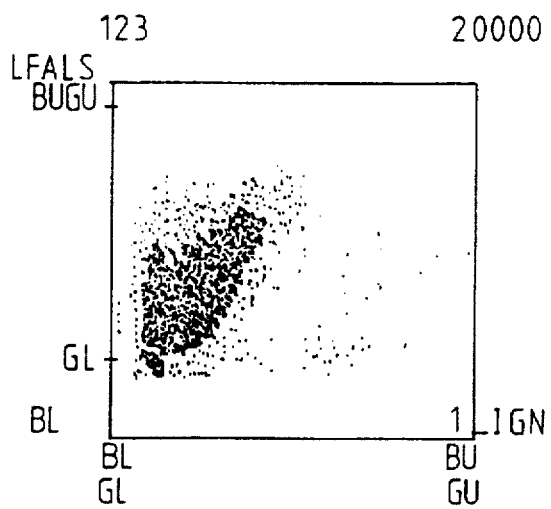
Figures 5A, 5B:
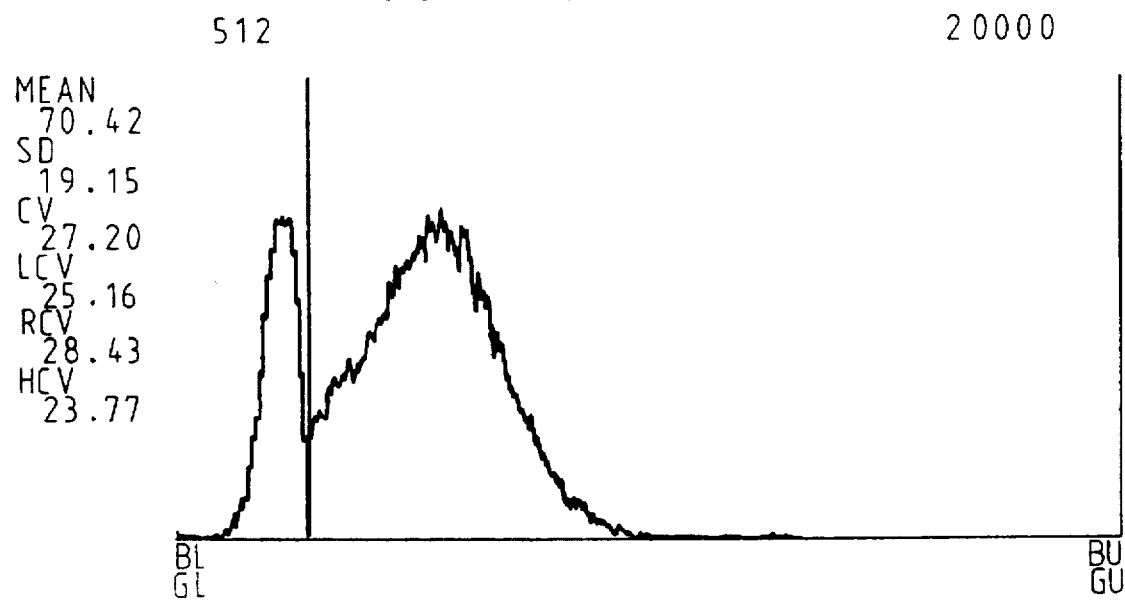
FIG. 5 depicts data that shows that protein C prevents PAC-1 binding to thrombocytes.

FIGS. 1–3 show the intensity of the fluorescence, i. e. the fibrinogen binding on stimulated thrombocytes as well as the size of the thrombocytes. FIG. 1 shows the fibrinogen binding in the PRP after ADP stimulation. The application of the agonist leads to a fibrinogen binding on the cell surface, but also to a change of the size of the thrombocytes. In comparison to this, FIG. 2 shows the fibrinogen binding after ADP stimulation in the presence of Protein C in a concentration that corresponds to the 4-fold plasma concentration. A significant reduction of the fibrinogen binding is recognizable. As opposed to this, activated Protein C in this test mixture leads to no decrease of the fibrinogen binding on thrombocytes.

Binding of PAC-1 on activated thrombocytes

The monoclonal antibody PAC-1 reacts with the glycoprotein IIb–IIIa complex on the surface of thrombocytes after activation of the thrombocytes with ADP.

The drawing of blood occurred in EDTA/Trasylol. Thereafter, platelet-enriched blood plasma (PRP) and plasma in which the blood platelets were depleted (PPP) was produced by conventional centrifugation. PRP was diluted 1:40 in PPP. Thereafter, PAC-1 was added with ADP and, optionally, Protein C or activated Protein C and incubated at room temperature for 10 minutes. After addition of an anti-mouse antibody (fluorescence conjugated, FITC from Sigma Chemical Co.) and a further incubation time of 20 minutes, the binding of the PAC-1 on thrombocytes was detected by flow cytometric examination.

FIG. 4

Binding of the PAC-1 to PRP/ADP

FIG. 5

The PAC-1 Binding to Thrombocytes is Prevented in the Presence of Protein C.

FIG. 6

Activated Protein C Leads to no Influencing of the PAC-1 Binding on ADP-stimulated Thrombocytes.

Blood Platelet Deposition on the Subendothelium in the Perfusion Experiment

Venous blood was anticoagulated with citrate-phosphate-dextrose (19 mM). Protein C (Immuno AG) was reconstituted and added to 20 ml of the anticoagulated blood before the perfusion. Perfusions were performed at 37° C. in a perfusion chamber (experimental description in Thromb. Haemost., 37, 1–16, 1977). Enzymatically-treated aorta samples from rabbit were mounted in a perfusion chamber. With the aid of a haemodialysis blood pump (Renal Systems, Minneapolis, Minn., USA) an appropriate flow rate was set. After 5 minutes of perfusion, the aorta samples were washed with buffer and fixed (glutaraldehyde: formaldehyde= 2%:3% (v/v). Thereafter, these were embedded in JB4 (Polyscience, Warrington, USA), stained with Toluidine Blue, and morphometrically examined. With the help of a computer program (described in Haemostasis, 16, 8–14, 1986), the blood platelets were classified as follows: adhesion (blood platelet layer<5 μm), thrombi (aggregation≧5 μm), both expressed in percent of the total length of the blood vessel. The results are given in Table 1. At concentrations of less than 16 μg/ml, Protein C demonstrates no effect on the adhesion of blood platelets in comparison to controls. At concentrations of 16 and 32 μg/ml, the covered surface was significantly reduced.

TABLE 1

Blood Platelet Deposition on Subendothelium in the Perfusion
Experiment with Citrate-anticoagulated Blood in Dependence on
the Protein C Concentration (n = 3, $\bar{x} \pm$ SD) (flow rate = 800 s$^{-1}$)

|  | coated surface | Adhesion | Clots |
| --- | --- | --- | --- |
| Control | 18.1 ± 5.3 | 9.3 ± 4.5 | 8.8 ± 1.9 |
| Protein C 16 µg/ml | 13.1 ± 3.5 | 4.8 ± 0.9 | 8.3 ± 2.9 |
| Protein C 32 µg/ml | 9.6 ± 5.7 | 4 ± 2.5 | 5.6 ± 3.4 |

We claim:

1. A method for preventing a thromboembolic condition caused by deposition or aggregation of blood components selected from the group consisting of thrombocytes, thrombocyte microparticles and leukocytes occurring on a vessel surface or endothelium of a patient, comprising the step of administering to said patient a pharmaceutical composition comprising native protein C in a zymogen form.

2. A method according to claim 1, wherein said deposition or aggregation of blood components occurs on a blood vessel or endothelium that has undergone injury, infection or an invasive procedure, or on exposed subendothelium or on an artificial vessel surface or a vessel prosthesis with or without endothelium.

3. A method according to claim 2, wherein said invasive procedure is selected from the group consisting of angioplasty, catheterization and insertion of a vessel prosthesis.

4. A method according to claim 1, wherein said thromboembolic condition is arterial restenosis.

5. A method for preventing deposition or aggregation of blood components selected from the group consisting of thrombocytes, thrombocyte microparticles and leukocytes occurring in a body fluid of a patient at an extracorporeal location, comprising the step of adding to said body fluid a pharmaceutical composition comprising native protein C in a zymogen form.

6. A method according to claim 5, wherein said extracorporeal location is a blood circulation apparatus, a dialysis apparatus or an artificial kidney.

7. A method for treatment of a thromboembolic condition caused by deposition or aggregation of blood components selected from the group consisting of thrombocytes, thrombocyte microparticles and leukocytes on a blood vessel surface or endothelium of a patient, comprising the step of administering a pharmaceutical composition to said patient comprising native protein C in a zymogen form.

8. A method according to claim 7, wherein said deposition or aggregation of blood components occurs on a blood vessel or endothelium that has undergone injury, infection or an invasive procedure, or on exposed subendothelium or on artificial vessel surfaces or a vessel prosthesis with or without endothelium.

9. A method according to claim 7, wherein said invasive procedure is selected from the group consisting of angioplasty, catheterization and insertion of a vessel prosthesis.

* * * * *

UNITED STATES PATENT AND TRADEMARK OFFICE
CERTIFICATE OF CORRECTION

PATENT NO.    : 5,614,493
DATED         : March 25, 1997
INVENTOR(S)   : Johann EIBL et al.

Figure 6A:
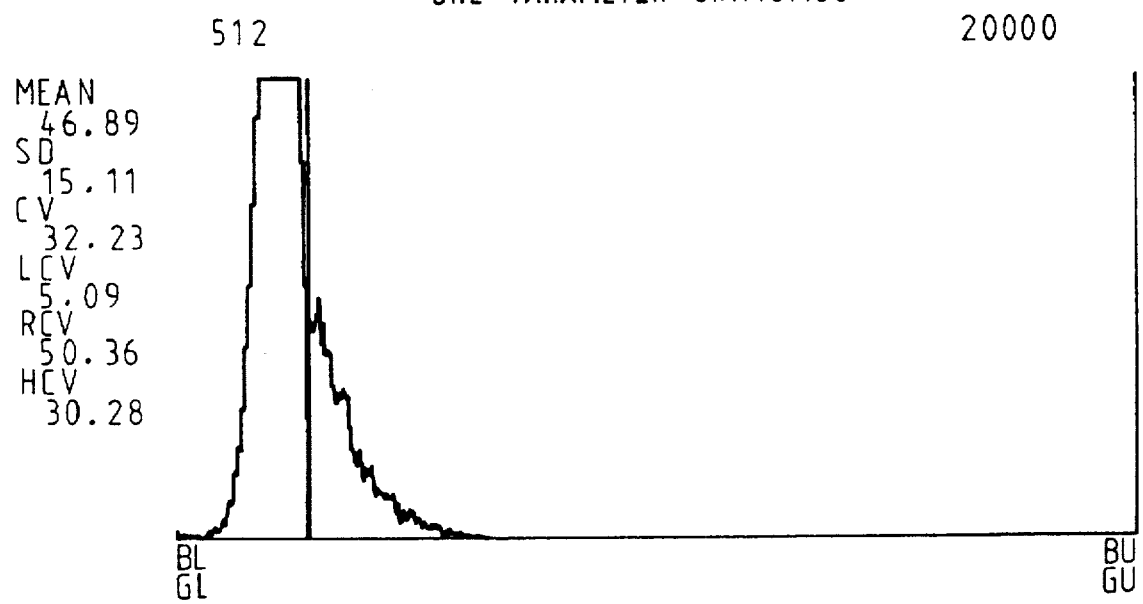
FIG. 6 depicts data that shows that activated protein C does not affect PAC-1 binding on thrombocytes stimulated with adenosine diphosphate.
Figure 6B:
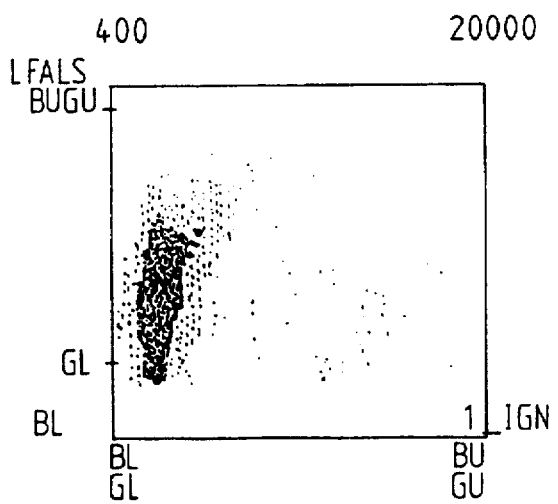

It is certified that error appears in the above-indentified patent and that said Letters Patent is hereby corrected as shown below:

On drawing sheet;

Please note that between Figures 6A and 6B, wherein

"JENNINGS-21 18/2/88 14 35

1P256 PETER 6

1LIGN        /LFALS" should be deleted.

Signed and Sealed this

Fifteenth Day of July, 1997

Attest:

BRUCE LEHMAN

Attesting Officer     Commissioner of Patents and Trademarks